US008257683B2

(12) United States Patent
Cantrell et al.

(10) Patent No.: US 8,257,683 B2
(45) Date of Patent: Sep. 4, 2012

(54) MULTICOMPONENT ASSEMBLIES HAVING ENHANCED BINDING PROPERTIES FOR DIAGNOSIS AND THERAPY

(75) Inventors: Gary L. Cantrell, Troy, IL (US); B. Daniel Burleigh, O'Fallon, MO (US)

(73) Assignee: Mallinckrodt LLC, Hazelwood, MO (US)

(*) Notice: Subject to any disclaimer, the term of this patent is extended or adjusted under 35 U.S.C. 154(b) by 312 days.

(21) Appl. No.: 12/603,402

(22) Filed: Oct. 23, 2009

(65) Prior Publication Data

US 2010/0041826 A1 Feb. 18, 2010

Related U.S. Application Data

(62) Division of application No. 11/462,591, filed on Aug. 4, 2006, now Pat. No. 7,713,514, which is a division of application No. 09/932,291, filed on Aug. 17, 2001, now Pat. No. 7,087,212.

(51) Int. Cl.
*A61K 51/00* (2006.01)
*A61M 36/14* (2006.01)

(52) U.S. Cl. ............... 424/1.65; 424/1.11; 424/1.69; 424/1.73

(58) Field of Classification Search ............ 424/1.11, 424/1.49, 1.53, 1.65, 1.69, 1.73, 9.1, 9.2, 424/9.3, 9.4, 9.5, 9.6, 9.7, 9.8; 534/7, 10–16; 530/300
See application file for complete search history.

(56) References Cited

U.S. PATENT DOCUMENTS

| 4,247,406 | A | 1/1981 | Widder et al. |
|---|---|---|---|
| 5,190,766 | A | 3/1993 | Ishihara |
| 5,312,617 | A | 5/1994 | Unger et al. |
| 5,510,118 | A | 4/1996 | Bosch et al. |
| 5,542,935 | A | 8/1996 | Unger et al. |
| 5,543,133 | A | 8/1996 | Swanson et al. |
| 5,552,133 | A | 9/1996 | Lambert et al. |
| 5,733,572 | A | 3/1998 | Unger et al. |
| 5,770,222 | A | 6/1998 | Unger et al. |
| 5,785,969 | A | 7/1998 | Magdassi et al. |
| 5,985,852 | A | 11/1999 | Nagy et al. |
| 6,001,335 | A | 12/1999 | Unger |
| 6,045,821 | A | 4/2000 | Garrity et al. |
| 6,331,289 | B1 | 12/2001 | Klaveness et al. |
| 6,524,552 | B2 | 2/2003 | Klaveness et al. |
| 6,610,269 | B1 | 8/2003 | Klaveness et al. |
| 7,087,212 | B2* | 8/2006 | Cantrell et al. ............ 424/9.1 |
| 7,713,514 | B2* | 5/2010 | Cantrell et al. ............ 424/1.65 |

FOREIGN PATENT DOCUMENTS

| WO | WO 90/04943 | 5/1990 |
|---|---|---|
| WO | WO 95/15979 | 6/1995 |
| WO | WO 96/40285 | 12/1996 |

OTHER PUBLICATIONS

Bischoff, Joyce, Perspectives Series: Cell Adhesion in Vascular Biology, Journal of Clinical Investigation, vol. 99, No. 3, Feb. 1997, pp. 373-376, 3 pages.
Fukuda et al., A Peptide Mimic of E-Selectin Ligand Inhibits Sialyl Lewis X-dependent Lung Colonization of Tumor Cells, Cancer Research, vol. 60, Jan. 15, 2000, pp. 450-456, 6 pages.
Kiessling et al., Chapter 29, Principles for Multivalent Ligand Design, Annual Reports in Medical Chemistry, vol. 35, 2000, pp. 321-330, 12 pages.
Lesley et al., CD44 in inflammation and metastasis, Glycoconjugate Journal, vol. 14, 1997, pp. 611-622, 12 pages.
Martens et al., Peptides Which Bind to E-selectin and Block Neutrophil Adhesion, The Journal of Biological Chemistry, vol. 270, No. 36, Sep. 8, 1995, pp. 21129-21136, 8 pages.
McEver et al., Leukocyte Trafficking Mediated by Selectin-Carbohydrate Interactions, The Journal of Biological Chemistry, vol. 270, No. 19, May 12, 1995, pp. 11025-11028, 4 pages.
McEver, Rodger P., Selectin-carbohydrate interactions during inflammation and metastasis, Glycoconjugate Journal, vol. 14, 1997, pp. 585-591, 7 pages.
Siegelman et al., Activation and interaction of CD44 and hyaluronan in immunological systems, Journal of Leukocyte Biology, vol. 66, Aug. 1999, pp. 315-321, 7 pages.
Torchilin et al., Preservation of Antimyosin Antibody Activity After Covalent Coupling to Liposomes, Biochemical and Biophysical Research Communications, vol. 89, No. 4, Aug. 28, 1979, pp. 1114-1119, 6 pages.
Zalipsky et al., Peptide Attachment to Extremities of Liposomal Surface Grafted PEG Chains: Preparation of the Long-Circulating Form of Laminin Pentapeptide, YIGSR, Bioconjugate Chemistry, vol. 6, 1995, pp. 705-708, 4 pages.
Zinn et al., Specific Targeting of Activated Endothelium in Rat Adjuvant Arthritis with A 99m Tc-Radiolabeled E-Selectin-Binding Peptide, Arthritis & Rheumatism, vol. 42, No. 4, Apr. 1999, pp. 641-649, 9 pages.
Allen et al., A new strategy for attachment of antibodies to sterically stabilized liposomes resulting in efficient targeting to cancer cells, Biochimica et Biophysica Acta, vol. 1237, 1995, pp. 99-108.
Andreoni et al., Tumour photosensitization by chemotherapeutic drugs, Biologia, vol. 3, 1993, pp. 43-46.
Babich et al., Technetium-99m-Labeled Chemotactic Peptides: Comparison with Indium-111-Labeled White Blood Cells for Localizing Acute Bacterial Infection in the Rabbit, The Journal of Nuclear Medicine, vol. 34, No. 12, Dec. 1993, pp. 2176-2181.
de Jong and Ten Cate, New ultrasound contrast agents and technological innovations, Ultrasonics, vol. 34, 1996, pp. 587-590.
Forsberg et al., Clinical applications of ultrasound contrast agents, Ultrasonics, vol. 36, 1998, pp. 695-701.

(Continued)

*Primary Examiner* — D L Jones

(57) ABSTRACT

An organized mobile multicomponent conjugate (OMMC) and method of using to enhance binding of weakly binding compounds to a target. A lamellar structure containing at least two binding compounds is assembled under conditions in which the binding compounds self-regulate in or on the lamellar structure, forming a cooperative ensemble that is capable of binding with enhanced affinity to a complementary affinity site on a target. Each binding compound is bound to the lamellar surface, and may be connected by a linker. The OMMC may contain an effector molecule, such as a diagnostic or therapeutic agent, for administration to a patent who is then diagnosed or treated using the effector molecule.

84 Claims, 3 Drawing Sheets

OTHER PUBLICATIONS

Fritzsch et al., Status of contrast media research in MRI, ultrasound and X-ray, European Radiology, vol. 2, 1992, pp. 2-13.

Goldberg, Ultrasound Contrast Agents, Clinical Diagnostic Ultrasound, vol. 3, 1993, pp. 35-45.

Goldberg et al., Ultrasound Contrast Agents: A Review, Ultrasound in Medicine and Biology, vol. 20, No. 4, 1994, pp. 319-333.

Haldemann et al., Somatostatin Receptor Scintigraphy in Central Nervous System Tumors: Role of Blood-Brain Barrier Permeability, The Journal of Nuclear Medicine, vol. 36, No. 3, Mar. 1995, pp. 403-410.

Hilpert, Contrast Agents in Diagnostic Ultrasound, Mosby Year Book, Rumack et al. (eds.), vol. 1, Chapter 3, 1992, pp. 30-42.

Hoey et al., Organic Iodine Compounds As X-Ray Contrast Media, International Encyclopedia of Pharmacology and Therapeutics, vol. 1, Chapter 2, Pergamon Press, Oxford and New York, 1971, pp. 23-131.

Klibanov et al., Targeting and ultrasound imaging of microbubble-based contrast agents, Magnetic Resonance Materials in Physics, Biology and Medicine, vol. 8, 1999, pp. 177-184.

Knight et al., Thrombus Imaging with Technetium-99m Synthetic Peptides Based upon the Binding Domain of a Monoclonal Antibody to Activated Platelets, The Journal of Nuclear Medicine, vol. 35, No. 2, Feb. 1994, pp. 282-288.

Kuby, Antigen-Antibody Interactions, Immunology, 2nd Edition, W.H. Freeman & Co., New York, 1994, Chapter 6, pp. 138-139.

Makdisi and Versland, Asialoglycoproteins as Radiodiagnostic Agents for Detection of Hepatic Masses and Evaluation of Liver Function, Targeted Diagnostic Therapy, vol. 4, Chapter 7, 1991, pp. 151-162.

Ophir and Parker, Contrast Agents in Diagnostic Ultrasound, Ultrasound in Medicine and Biology, vol. 15, No. 4, 1989, pp. 319-333.

Palma and Bertolotto, Introduction to ultrasound contrast agents: physics overview, European Radiology, vol. 9, Suppl. 3, 1999, pp. S338-S342.

Tenenbaum et al., Radiolabeled Somatostatin Analog Scintigraphy in Differentiated Thyroid Carcinoma, The Journal of Nuclear Medicine, vol. 36, No. 5, May 1995, pp. 807-810.

Tilcock et al., Liposomal Gd-DTPA: Preparation and Characterization of Relaxivity, Radiology, vol. 171, No. 1, Apr. 1989, pp. 77-80.

EPO, Supplementary European Search Report, EP Application No. 02761334.8-2123, PCT/US0225582, mailed on Oct. 19, 2005, 5 pg.

* cited by examiner

MULTICOMPONENT ASSEMBLIES HAVING ENHANCED BINDING PROPERTIES FOR DIAGNOSIS AND THERAPY

This application is a Divisional of U.S. patent application Ser. No. 11/462,591, filed Aug. 4, 2006 now U.S. Pat. No. 7,713,514, which is a Divisional of U.S. patent application Ser. No. 09/932,291, filed Aug. 17, 2001 now U.S. Pat. No. 7,087,212, each of which is expressly incorporated by reference herein.

FIELD OF THE INVENTION

This invention pertains to methods and compositions for enhanced targeted binding to selectively deliver diagnostic and therapeutic agents to target tissues and organs.

BACKGROUND OF THE INVENTION

Non-covalent intermolecular forces (e.g., electrostatic, hydrogen bonding and van der Waals interactions) play a vital role in many biological processes. Examples of such processes include enzyme catalysis, drug-receptor interaction, antigen-antibody interaction, biotin-avidin interaction, DNA double helix formation, phagocytosis, pigmentation in plants and animals, and cellular transport.

Targeted delivery of medically useful molecules is well known and has been successfully applied in diagnostic and therapeutic applications. In conventional bioconjugate chemistry, almost all of the conjugates are prepared by covalent attachment of various effector molecules, such as drugs, dyes, hormones, magnetic resonance imaging agents, echogenic agents, radiopharmaceuticals, or chemotherapeutic agents, to bioactive carriers, such as antibodies, peptides and peptidomimetics, carbohydrates, or small molecule receptor agonists and antagonists. For example, in diagnostic medicine, various radionuclide and radionuclide chelates covalently attached to antibodies, hormones, peptides, peptidomimetics, and the like have been used to detect lesions such as tumors, inflammation, ischemia, and thrombi (Tenenbaum et al., Radiolabeled somatostatin analog scintigraphy in differentiated thyroid carcinoma, *J. Nucl. Med.*, 1995, 36, 807-810; Haldemann et al., Somatostatin receptor scintigraphy in central nervous system tumors: Role of blood-brain barrier Permeability. *J. Nucl. Med.*, 1995, 36, 403-410; Babich et al., Technetium-99m-labeled chemotactic peptides: Comparison with indium-111-labeled white blood cells for localizing acute bacterial infection in the rabbit. *J. Nucl. Med.*, 1993, 34, 2176-2181; Knight et al., Thrombus imaging with technetium-99m-labeled synthetic peptides based upon the binding domain of a monoclonal antibody to activated platelets. *J. Nucl. Med.*, 1994, 35, 282-288). Thus, the target site may be cells such as tumor cells, platelets, erythrocytes, leukocytes, macrophages, vascular endothelial cells, myocardial cells, hepatocytes, etc., or the extracellular matrix surrounding these cells.

In addition to the direct administration of biologically active compounds into the body, molecules such as these have also been encapsulated within organized amphiphilic aggregates such as a liposome, vesicle, or other multilamellar structures. The aggregates are then delivered to the particular organs or tissues of interest (U.S. Pat. Nos. 5,985,852; 5,785,969; and 5,542,935).

A requirement for targeted delivery is a strong interaction between the binding compound or targeting moiety (e.g., ligand) and the target or site of attachment (e.g., receptor) in the formation of a complex (e.g., ligand receptor complex). The dissociation constant ($K_d$) value of the complex should typically be in the nanomolar range. Compounds exhibiting $K_d$ values from about 100 nM and upward are considered weak binding compounds and are not generally considered to be useful for targeted imaging and therapeutic applications. However, there are many in vivo biological processes that do operate using multiple weak-binding interactions. These include, for example, enzyme-substrate complexes and cell adhesion molecules, which operate in the micromolar binding range. Cell adhesion molecules such as E, P, and L selectins are important biological modulators implicated in inflammatory and thrombolytic processes. (McEver, Selectin-carbohydrate interactions during inflammation and metastasis, *Glycoconj. J.*, 1997, 14(5), 585-91; McEver et al., Leukocyte trafficking mediated by selectin-carbohydrate interactions, *J. Biol. Chem.*, 1995, 270(19), 11025-8; Bischoff, Cell adhesion and angiogenesis. *J. Clin. Invest.*, 1997, 100 (11 Suppl), S37-39; Lesley et al., CD44 in inflammation and metastasis, *Glycoconj. J*, 1997, 14(5), 611-22; Siegelman et al., Activation and interaction of CD44 and hyaluronin in immunological systems. *J. Leukoc. Biol.*, 1999, 66(2), 315-21).

Previous work in this area involved the use of only high-binding ligands (Torchilin et al., Preservation of antimyosin antibody activity after covalent coupling to liposomes, *Biochem. Biophys. Res. Commun.*, 1979, 89(4), 1114-9; Allen et al., A new strategy for attachment of antibodies to sterically stabilized liposomes resulting in efficient targeting to cancer cells. *Biochim. Biophys. Acta*, 1995, 1237, 99-108; Zalipsky et al., Peptide attachment to extremities of liposomal surface grafted PEG chains: preparation of the long-circulating form of laminin pentapeptide, YIGSR. *Bioconjug. Chem.*, 1995, 6(6), 705-8). Although increased binding was observed in this system, a cooperative effect was not needed because the ligand was already endowed with sufficient affinity for targeting purposes. In contrast, weakly binding ligands presented a formidable challenge.

There is considerable effort to improve the binding affinity of relatively weakly binding selectins and selectin mimics, and to attach them covalently to effector molecules for imaging and therapeutic purposes (Fukuda et al., Peptide mimic of E-selectin ligand inhibits sialyl Lewis X-dependent lung colonization of tumor cells, *Cancer Research*, 2000, 60, 450-456). However, such efforts usually involve synthesizing and screening large numbers of new chemical entities to discover the ones that exhibit substantially improved binding properties. Furthermore, simple conjugation of effector moieties to an already weakly binding carrier is expected to result in a bioconjugate whose bioactivity is either greatly diminished or obviated altogether. Thus, there is a need for a simple method to enhance the affinity of any weakly binding targeted molecules in order to enhance their usefulness for diagnostic and/or therapeutic purposes.

SUMMARY OF THE INVENTION

The invention is directed to compositions and methods that enhance binding of a compound, particularly a weakly binding compound, to its target site in a patient.

An organized mobile multifunctional conjugate (OMMC) assembly is prepared and provided to a patient. The OMMC assembly is prepared by anchoring at least two binding compounds to a lamellar structure. In one embodiment, one binding compound is an anionic compound, and another binding compound is a saccharide, and the lamellar structure is a liposome, microsphere, micelle, etc. The binding compounds incorporated into the lamellar structure are mobile, and self-adjust relative to each other to form an OMMC ensemble. The OMMC ensemble binds to a target that contains at least two complementary affinity sites for the binding compounds. An agent, also called an effector molecule, may be attached to and/or contained within the lamellar structure to provide a targeted diagnostic and/or therapeutic agent to a patient to whom the OMMC is administered.

These and other advantages of the inventive compounds and methods will be apparent in light of the following figures, description, and examples.

DETAILED DESCRIPTION

Figure 1:
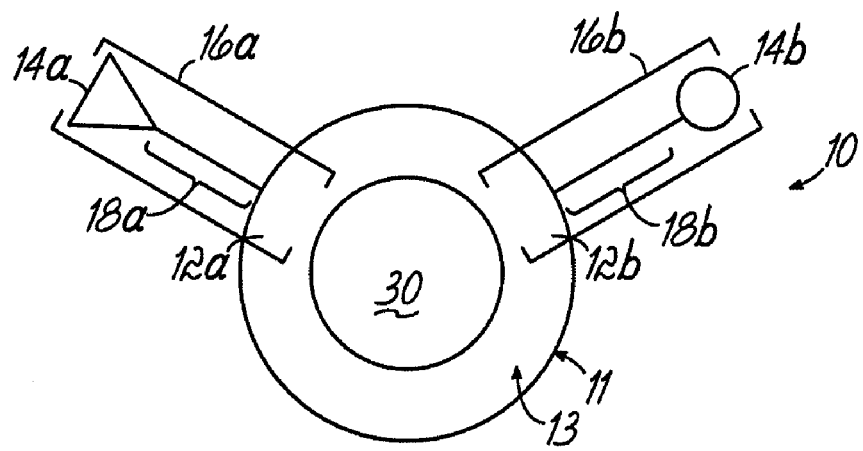
FIG. 1 is a schematic illustration of the general structure of an organized mobile multifunctional conjugate (OMMC) assembly.

In non-covalent interactions, although the free energy of association per unit interaction is quite small (less than about 40 kJ/interaction), the cumulative effect of multiple points of interaction along two surfaces can be substantial. This can lead to strong specific binding between the binding entities. Enhancement of binding due to the cooperative effect of multiple binding domains between two interacting units is well known in biological chemistry. For example, the multivalence of most antigens leads to a synergistic effect, in which the binding of two antigen molecules by antibody is greater than the sum of the individual antigen-antibody links (J. Kuby, *Immunology*, 2$^{nd}$ Edition, 1994, W.H. Freeman & Co., New York, pp. 138-139).

In the invention, enhanced binding of a binding compound that binds weakly (that is, a $K_d$ of about 100 nM or higher) to a target is achieved using a multicomponent assembly. Specifically, an organized mobile multifunctional conjugate (OMMC) assembly is prepared by anchoring at least two binding compounds to a lamellar structure. In one embodiment, the binding compounds are an anionic compound and a saccharide, and the lamellar structure is a liposome, microsphere, micelle, etc. The OMMC assembly is provided to a patient. The binding compounds incorporated into the lamellar structure are mobile, and self-adjust relative to each other to form an OMMC ensemble, which binds to a target that contains at least two complementary affinity sites for the binding compounds.

"Organized" refers to assemblies which are capable of assuming close to an optimum configuration on an assembly surface for binding at particular sites of interaction. "Mobile" refers to the degree of freedom within the assembly to allow complementary binding compounds or components to move independently within the lamellar structure with respect to each other to assume the optimum configuration. "Multifunctional conjugate" refers to two or more amphiphilic components that each contain a binding compound for a target complementary affinity site. The binding compounds of the ensemble cooperatively bind to the target with enhanced binding affinity, without the specific binding regions being contained within a single molecule. Furthermore, binding compounds in the inventive ensemble, constructed so that they express over a volume of space occupied outside of the ensemble, move within this space to interrogate the space until they find their respective binding complements.

An agent or effector molecule, for example, a contrast agent, may be attached to and/or contained within the lamellar structure to provide targeted delivery of the agent in a patient to whom the OMMC assembly is administered. Enhanced binding of these binding compounds may be exploited for diagnostic and therapeutic purposes.

The invention overcomes problems presented by weakly binding compounds by using novel OMMC assemblies. These dynamic self-adjusting OMMC assemblies allow increased targeting specificity and affinity of the binding compound to affinity sites in the target, particularly in comparison with an aggregate of individual active binding components.

The invention is also related to using the described OMMC assemblies for delivering effector molecules to the target tissues or organs for diagnostic and/or therapeutic purposes. Appropriate OMMC assemblies that contain a diagnostic and/or therapeutic agent or effector molecule attached to, incorporated within, or contained within the lamellar structure are prepared. Two or more binding compounds are incorporated on or into the surface of the OMMC assemblies. The OMMC assemblies are administered in an effective amount to a patient, and the binding compounds move about in or on the surface and self-adjust their relative positions and configurations in or on the assembly to bind to affinity sites at a target. A diagnostic or therapeutic procedure is thereafter performed on the patient. The procedure may use an imaging technique, for example, X-ray, computed tomography (CT), positron emission tomography (PET), magnetic resonance (MR), ultrasound, optics or radiography. The procedure may also be an in vitro diagnostic procedure, or a chemo-, photo-, or radiotherapeutic procedure, using methods known in the art.

One advantage of the present invention is that it does not require high-binding molecules to achieve a cooperative effect.

The general structure of an OMMC assembly 10 is shown in FIG. 1. A lamellar structure 13, the outer surface forming a type of surrounding shell 11, contains binding compounds 16a, 16b. The binding compounds 16a, 16b may be a ligand, an antibody, a peptide, a peptidomimetic, a carbohydrate, or a small molecule receptor agonist or antagonist ligand. In the lamellar structure 13 are regions 12a, 12b that incorporate the binding compounds 16a, 16b on or in the assembly 10. The binding compounds 16a, 16b contain binding regions or epitopes 14a, 14b. These epitopes 14a, 14b may individually have weak binding and bind to a target only through a cooperative effect. Flexible linkers 18a, 18b connect or tether the binding regions 14a, 14b to the anchoring regions 12a, 12b.

Anchor regions 12a, 12b are hydrophobic and self-assemble to minimize its aspect relative to the aqueous phase. Anchor regions 12a, 12b may be the same or different, and may be one or more of $CH_3(CH_2)_a$—W, $CF_3(CH_2)_a$—W, $CF_3(CF_2)_a$—W, $CF_3(CF_2)_a CH_2 CH_2$—W, $CH_3(CH_2)_a$—O—$(CH_2)_b$—W, $CF_3(CF_2)_a$—O—$(CH_2)_b$—W, $CH_3(CH_2)_a$—S—$(CH_2)_b$—W, or $CH_3(CH_2)_a$—S—S—$(CH_2)_b$—W, and $R^1O_2CCH_2(CHW)CO_2R^1$, wherein a and b range from 16 to 32, W is a connector unit of —O—, —CO—, —CO$_2$—, —OCO—, O$_2$CO—, —S—, —SO—, —SO$_2$—, —OSO—, —OSO$_2$—, —NH—, —NHCO—, —NHCS, —NHSO$_2$—, —PO$_2$—, —OPO$_2$—, —PO$_2$H—, or —OPO$_2$H—, and R is a normal alkyl radical containing 16 to 24 carbon atoms. Other hydrophobic material may also be contained within the anchor regions 12a, 12b.

Binding regions 14a, 14b are hydrophilic and are solvated with an aqueous phase. Binding regions 14a, 14b may be the same or different, and may be amino acids, peptides, and peptidomimics; mono-, di-, and oligosaccharides, such as C or O monosaccharides and glycosides, C or O glucosides, glucose, galactose, fucose, glycomimics, and glycopeptides; sialic acid, carminic acid, or anionic compounds of —$(CH_2)_d$—$CO_2$—, —$(CH_2)_d$—$SO_3$—, —$(CH_2)_d$—$OSO_3$—, —$(CH_2)_d$—$PO_3$=, —$(CH_2)_d$—$OPO_3$=, —Ar—$SO_3$—, DTPA, EDTA, DOTA, or EGTA, where d ranges from 1 to 10.

Linkers 18a, 18b may be the same or different, and may be polysorbates, polyglycerols, polypeptides, polynucleotides, polysaccharides, polyvinylpyrrolidones, polyvinylalcohols, polyethyleneglycols such as polyethythene glycols having a molecular weight in the range of 1,000 to 4,000, polyglycolate, polylactate, or copolymers derived from any of the above groups.

The lamellar structure 13 may be $CH_3$—$(CH_2)_e$—X, $CH_3$—$(CF_2)_e$—X, $CF_3$—$(CF_2)_e$—X, $CF_3$—$(CF_2)_f$—O—$(CH_2)_g$—X, $CH_3$—$(CH_2)_f$—S—$(CH_2)_g$—X, $CH_3$—$(CH_2)_f$—S—S—$(CH_2)_g$—X, $CH_3$—$(CH_2)_g CO_2(CH_2)_h$—X, $CH_3$—$(CH_2)_f CONH(CH_2)_g$—X, $CH_3$—$(CH_2)_f NHCONH(CH_2)_g$—X, $CH_3$—$(CH_2)_f OCONH(CH_2)_g$—X, $CH_3$—$(CH_2)_1 NH(CH_2)_g$-X, $CH_3$—$(CH_2)_f NRCH_2)_g$—X, $CH_3$—$(CH_2)_f SO(CH_2)_g$—X, $CH_3$—$(CH_2)_f SO_2(CH_2)_g$—X, $CH_3$—$(CH_2)_m NH(CH_2)_f CO_2(CH_2)_g$—X, $CH_3(CH_2)_f]_2 N(CH_2)_g CONH(CH_2)_h$—X  $R^2 O_2 CCH_2(CHY)CO_2 R^2$ and/or $R^2 O_2 CCH_2 CH_2(CHY)CO_2 R^2$; where $R^2$ is a normal alkyl radical containing 16 to 24 carbon atoms, e ranges from 16 to 32, f, g, and h range from 1 to 15, X is carboxylate, sulfonate, sulfate, phosphate, or phosphonate, Y is —$(CH_2)_k$—X, —$OCO(CH_2)_k$—X, —$NHCO(CH_2)_k$—X, or —$CH_2 OCO(CH_2)_2$—$CO_2$-, and k is 2 to 6. The lamellar structure 13 may also be salts of docosanoic, tetracosanoic, hexacosanoic, octacosanoic, and triacontanoic acids.

The various chemical compositions of the anchor regions, binding regions, linkers, and lamellar structure are as listed in the following tables.

TABLE 1

| Anchors |
| --- |
| A1 and/or A2 (12a or 12b) |
| $CH_3(CH_2)_a$—W |
| $CF_3(CH_2)_a$—W |
| $CF_3(CF_2)_a$—W |
| $CF_3(CF_2)_a CH_2 CH_2$—W |
| $CH_3(CH_2)_a$—O—$(CH_2)_b$—W |
| $CF_3(CF_2)_a$—O—$(CH_2)_b$—W |
| $CH_3(CH_2)_a$—S—$(CH_2)_b$—W |
| $CH_3(CH_2)_a$—S—S—$(CH_2)_b$—W |
| $R^1 O_2 CCH_2(CHW)CO_2 R^1$ |
| W |
| —O— |
| —CO— |
| —$CO_2$— |
| —$O_2 C$— |
| —OCO— |
| —$O_2 CO$— |
| —S— |
| —SO— |
| —OSO— |
| —$OSO_2$— |
| —$SO_2$— |
| —$OPO_2 H$— |
| —NH— |
| —NHCO— |
| —NHCS— |
| —$NHSO_2$— |
| —$PO_2 H$— |

TABLE 1-continued

| Anchors |
| --- |
| —$PO_2$— |
| —$OPO_2$— | a, b = 16-32

$R^1$ is a normal alkyl radical containing 16-24 carbon atoms.

TABLE 2

| Binding Region (Epitopes) | |
| --- | --- |
| B1 and/or B2 (14a, 14b) | |
| amino acids | |
| peptides (1-20 amino acids) | |
| peptidomimics | |
| monosaccharides | |
| oligosaccharides (1-10) | |
| glycomimics | |
| glycopeptides | |
| anionic compounds such as: | |
| —$(CH_2)_d$—$CO_2^-$ | |
| —$(CH_2)_d$—$SO_3^-$ | |
| —$(CH_2)_d$—$OSO_3^-$ | |
| —$(CH_2)_d$—$PO_3^-$ | |
| —$(CH_2)_d$—$OPO_3^-$ | |
| —Ar—$SO_3^-$ | |
| DTPA | |
| EDTA | |
| DOTA | |
| EGTA | |
| C- or O- monosaccharides and glycosides such as: | |
| glucose | |
| mannose | |
| fucose | |
| galactose | |
| glucosamine | |
| mannosamine | |
| galactosamine | |
| sialic acid | |
| flavonoids | |
| isoflavonones | |
| C- or O- glucosides such as, but not limited to: | |
| rutin | |
| neohesperidin dihydrochalone | |
| phloridizin | |
| hesperidin | |
| hesperidin methyl chalcone | |
| naringenin | |
| esculin | |
| carminic acid family including, but not limited to, carmine, 18b-glycyrrhetinic acid and salt | |
| B1 | B2 |
| oligosaccharide derived from the glycan family of carbohydrate including, but not limited to: | —$O(CH_2)_{1or2}CO_2^-$ |
| hyaluronic acid | —$O(CH_2)_{1or2}SO_3^-$ |
| heparin | —$O(CH_2)_{1or2}SO_4^-$ |
| chondroitin sulfate | —$O(CH_2)_{1or2}PO_4^-$ |
| dermatan | |
| mono or disaccharide including, but not limited to: | |
| galactose | |
| fucose | |
| glucose | |
| mannose | |
| hyaluronic acid | | d = 1-10

TABLE 3

Lamellar Structure $CH_3—(CH_2)_e—X$
$CH_3—(CF_2)_e—X$
$CF_3—(CF_2)_e—X$
$CF_3—(CF_2)_f—O—(CH_2)_g—X$
$CH_3—(CH_2)_f—S—(CH_2)_g—X$
$CH_3—(CH_2)_f—S—S—(CH_2)_g—X$
$CH_3—(CH_2)_gCO_2(CH_2)_h—X$
$CH_3—(CH_2)_fCONH(CH_2)_g—X$
$CH_3—(CH_2)_fNHCONH(CH_2)_g—X$
$CH_3—(CH_2)_fOCONH(CH_2)_g—X$
$CH_3—(CH_2)_fNH(CH_2)_g—X$
$CH_3—(CH_2)_fN[(CH_2)_g]_2—X$
$CH_3—(CH_2)_fSO(CH_2)_g—X$
$CH_3—(CH_2)_fSO_2(CH_2)_g—X$
$CH_3—(CH_2)_mNH(CH_2)_fCO_2(CH_2)_g—X$
$CH_3—[(CH_2)_f]_2N(CH_2)_gCONH(CH_2)_h—X$ e = 16-32
f, g, h = 1-15
X = carboxylate, sulfonate, sulfate, phosphate, phosphonate salts of:

docosanoic acid
tetracosanoic acid
hexacosanoic acid
octacosanoic acid
triacontanoic acid
$R^2O_2CCH_2(CHY)CO_2R^2$
$R^2O_2CCH_2CH_2(CHY)CO_2R^2$ $R^2$ is a normal alkyl radical containing 16-24 carbon atoms
$Y = —(CH_2)_k—X, —NHCO(CH_2)_k—X,$
$—OCO(CH_2)_k—X, —CH_2OCO(CH_2)_2—CO_2^-$ k = 1-6
X = carboxylate, sulfate, phosphate

TABLE 4

Linkers
L1 and/or L2 (18a, 18b)

polysorbates
polyglycerols
polypeptides
polynucleotides
polysaccharides
polyvinylpyrrolidones
polyvinylalcohols
polyethyleneglycols
polyglycolate
polylactate
poly(ethyleneglycol)$_p$ (p = 40-150)

In one embodiment of the invention, OMMC assemblies 10 have the general structure shown in FIG. 1 where anchors 12a, 12b may be the same or different and are selected from the group or groups consisting of $CH_3(CH_2)_a$—W, wherein a ranges from 16 to 24 and W is a connector unit selected from the group consisting of —O—, —CO—, —CO$_2$—, —OCO—, —S—, —SO—, —SO$_2$—, —OSO$_2$—, —NH—, —NHCO—, —NHCS—, —NHSO$_2$—, —PO$_2$H—, or —OPO$_2$H—. Binding regions 14a, 14b may be the same or different and are selected from the group consisting of C or O monosaccharides and glycosides, with oligosaccharides containing 1 to 10 furanose or pyranose units, amino acids, or peptides containing 1 to 20 amino acid residues, flavonoids and Isoflavonones, C— or O— glucosides (rutin, neohesperidin dihydrochalone, phloridizin, hesperidin, hesperidin methyl chalcone, naringenin, esculin); carminic acid family members including, but not limited to, carmine, 18b-glycyrrhetinic acid and salts. Linkers 18a, 18b may be the same or different and are selected from the group consisting of polyethyleneglycols, polyglycolate, and polylactate. Lamellar structure 13 is selected from the group consisting of $CH_3$—$(CH_2)_e$—X, wherein e ranges from 16 to 32, and X is selected from the group consisting of carboxylate, sulfonate, sulfate, phosphate, and phosphonate.

In another embodiment of the invention, OMMC assemblies 10 have the general structure as shown in FIG. 1, where binding region 14a is an oligosaccharide derived from the glycan family of carbohydrates that includes, but is not limited to, hyaluronic acid, heparin, chondroitin sulfate, and dermatan, or a mono- or disaccharide including, but not limited to, galactose, fucose, glucose, mannose, or hyaluronic acid. In this embodiment, binding region 14b is selected from the group consisting of —O(CH$_2$)$_1$ or $_2$CO$_2$—; —O(CH$_2$)$_1$ or $_2$SO$_3$; —O(CH$_2$)$_1$ or $_2$ SO$_4$—; —O(CH$_2$)$_1$ or $_2$PO$_4$—. Linkers 18a, 18b are selected from the group consisting of poly(ethyleneglycol)$_p$ with p between 40 and 150 units. Lamellar structure 13 is selected from the group consisting of salts of docosanoic, tetracosanoic, hexacosanoic, octacosanoic and triacontanoic acid.

Figure 2:
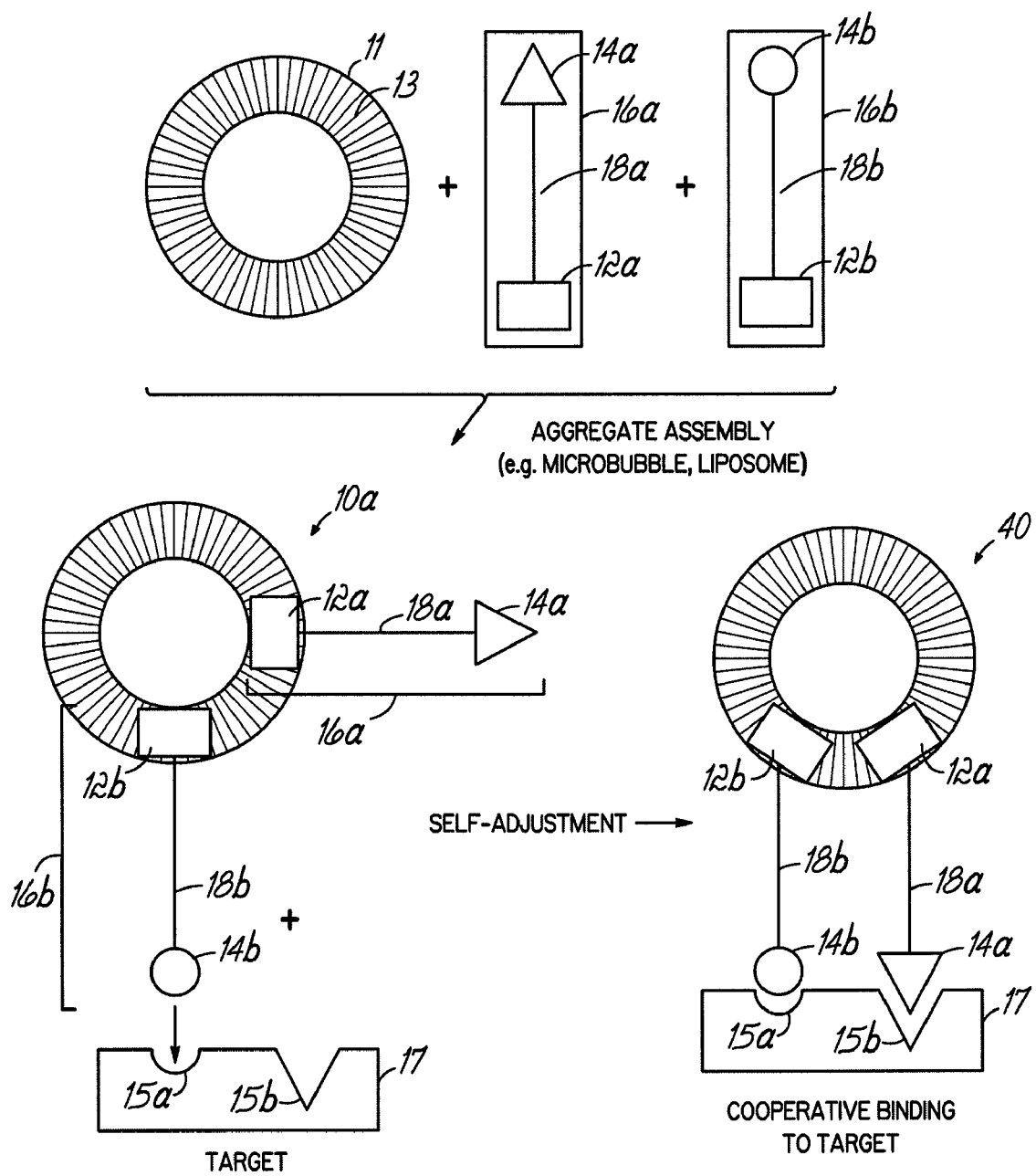
FIG. 2 is a schematic illustration of the steps in forming and binding an OMMC ensemble to a target.
Figure 3:
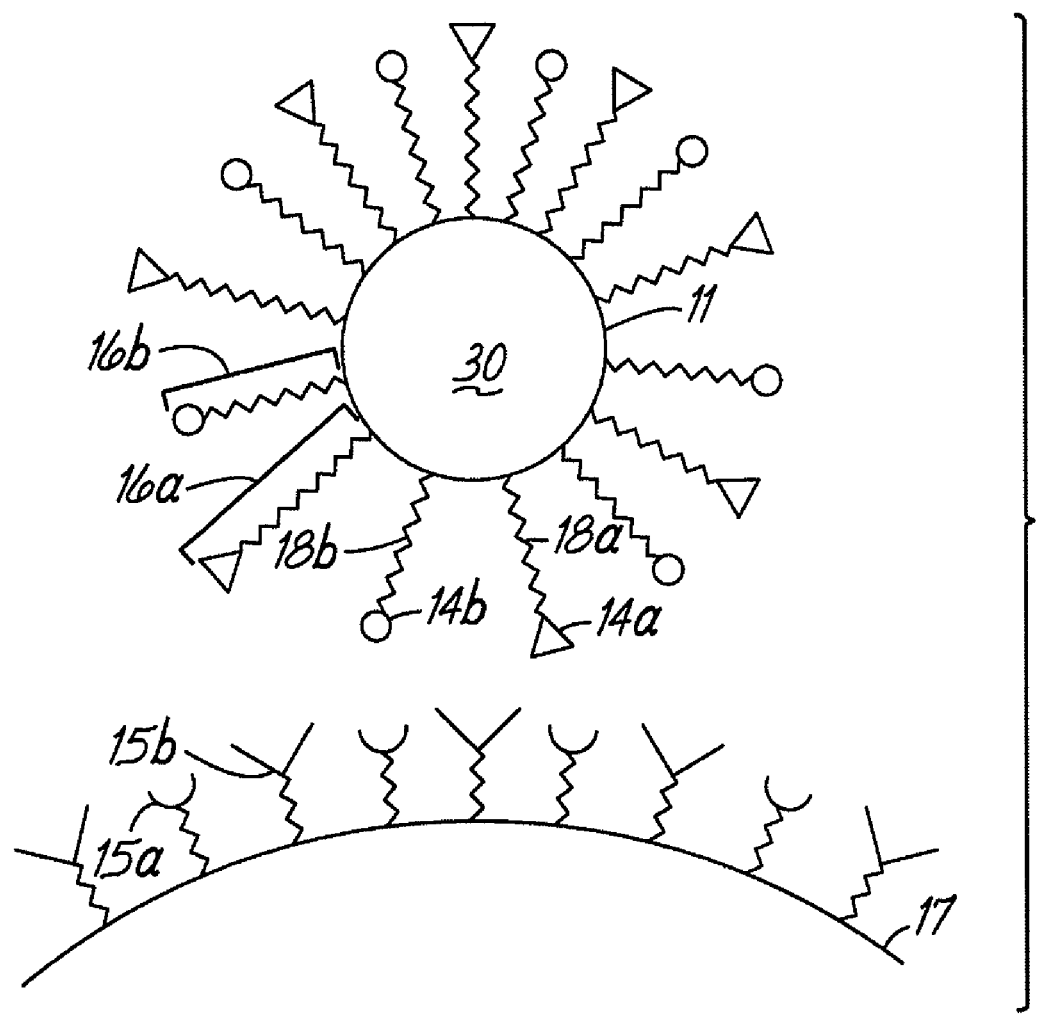
FIG. 3 is a schematic two-dimensional illustration of an OMMC ensemble binding to a target.

Enhancement of the affinity of weakly binding compounds 16a, 16b is accomplished according to the following method, as schematically illustrated in FIGS. 2 and 3. Two or more binding compounds 16a, 16b, such as weakly binding compounds, are added to the lamellar structure 13 to form an OMMC assembly 10a. The binding compounds 16a, 16b are initially randomly distributed throughout the lamellar structure 13.

The binding compounds 16a, 16b on assembly 10, in the presence of the complementary affinity sites 15a, 15b on the target 17, move about the lamellar structure in or on the surface and self-adjust their relative positions and configurations by differential movement to produce an optimized ensemble structure 40, bound to complementary affinity sites 15a, 15b, such as receptors. The mobility of the binding compounds 16a, 16b in and on the OMMC assembly 10a is similar to the differential motion of amphiphilic molecules within a cell membrane surface. Optimum binding occurs by an approach to equilibrium process. All components of the OMMC assembly 10 have a dynamic motion, both up and down and side to side. In addition, linkers 18a, 18b act as tethers and can also "float" within a given volume of space over the surface of the assembly 10 in the aqueous phase. If an expressed region of a target 17 having many affinity sites 15a, 15b is encountered, multiple bindings start to occur and a dynamic equilibrium is established: as one set of binding compounds 16a, 16b detach, another set of binding compounds 16c, 16d (not shown) adjacent to binding compounds 16a, 16b are within a spatial distance to attach. At a point, the number of attachments to a target 17 is sufficient to halt motion of the assembly 10, essential "locking" it onto the target 17. The binding compounds (e.g., ligands) 16a, 16b in the optimized assembly 10 then bind via their binding regions 14a, 14b, in a cooperative fashion, to their respective epitopes in receptors 15a, 15b of target 17. Thus, the binding domains 14a, 14b, which individually may have weak interaction with a given target surface, form a self-optimizing composition, resulting in greatly increased binding and targeting effectiveness.

As previously stated, the OMMC assembly 10 can accommodate various effector molecules 30. Effector molecules 30 include, for example, fluids (e.g., a gas or liquid fluorocarbon or superheated fluid) useful for ultrasonic procedures, fluorescent compounds useful for biomedical optical procedures, paramagnetic agents useful for magnetic resonance imaging procedures, radionuclides for nuclear medicine applications such as I-123, I-131, Tc-99m, Re-186, Re-188, SM-152, Ho-155, Bi-202, and Lu-177, and X-ray opacification agents for X-ray or computed tomography procedures. Examples of each of these effector molecules and their effective doses and uses are well known to those of skill in the art as described in, for example, Fritzsch et al., Eur. Radiol. 2, 2-13(1992); Rubaltelli, Photodiagnostic and Phototherapeutic Techniques in Medicine, in Documento Editoriale, G. Joni and C. Perria (Eds.), Milano, 1995, 101-107; Andreoni et al., Tumour Photosensitization by Chemotherapeutic Drugs, Biologia, 1993, No. 3, 43-6; Knoefel, I.E.P. T. Section 76, Vol. 1, Pergamon Press, Oxford and New York, 1971, Chapter 2: Organic Iodine Compounds as X-ray Contrast Media; Rumack et al., Diagnostic Ultrasound, Vol. 1, Mosby Year Book, St. Louis, Chapter 3, Contrast Agents in Diagnostic Ultrasound, 30-42 (1992); Forsberg et al., Ultrasonics 1998, Clinical Applications of Ultrasound Contrast Agents, February, 36(1-5):695-701; Goldberg et al., Ultrasound Med. Biol. 1994, 20(4): 319-33, Ultrasound Contrast Agents: A Review; deJong and Ten Cate, Ultrasonics 1996 Jun, 34(2-5):587-90, New Ultrasound Contrast Agents and Technological Innovations; Goldberg, Clin. Diag. Ultrasound 1993, 28: 35-45, Ultrasound Contrast Agents; Dalla Palma and Bertolotto, Eur. Radiol.,1999, Suppl 3:S338-42, Introduction to Ultrasound Contrast Agents: Physics Overview; Ophir and Parker, Ultrasound Med. Biol. 1989, 15(4):319-33, Contrast Agents in Diagnostic Ultrasound; Klibanov et al., MAGMA 1999 Aug., 8(3):177-184, Targeting and Ultrasound Imaging of Microbubble-Based Contrast Agents; Makdisi and Versland, Targeted Diag. (New) Ther. 1991, 4:151-162, Asialoglycoproteins as Radiodiagnostic Agents for Detection of Hepatic Masses and Evaluation of Liver Function; WO 9004943; U.S. Pat. No. 5,312,617; Tilcock et al., Radiology 1989, 171: 77-80, Liposomal Gd-DTPA: Preparation and Characterization of Relaxivity, each of which is expressly incorporated by reference herein in its entirety.

The dose of effector molecules depends on the type of imaging or therapy being performed (nuclear, optical, magnetic resonance, ultrasound, optical acoustic or X-ray contrast). In general, the doses necessary for these procedures vary. For examples, for nuclear imaging, depending on the type of emission, only a few micrograms are necessary. Optical imaging agents require tens to hundreds of milligrams for a human dose. Ultrasound imaging requires about 0.2 to $10 \times 10^{19}$ microbubbles/mL, with a typical dose of around 1 mL (stabilized with a few milligrams of composite) of the described formulations; in one embodiment 250 µL was used. Magnetic resonance imaging typically requires 50 to 1000 milligram doses in solution of metal chelates. X-ray contrast imaging requires several grams of material in solution for opacification. In one embodiment, targeted X-ray contrast imaging of the liver is performed, with the effector molecules taken up by the hepatic cells.

The effector molecule 30 can be attached, either directly or indirectly, to the assembly 10 or contained within the assembly 10. For example, an echogenic agent and/or MRI agent may be a fluid contained within the void of the assembly 10. A radionuclide, optical and/or cytotoxic agent may be anywhere in the assembly 10 (in the void, or on binding compound 16a, 16b). A chemotherapeutic agent in the assembly 10 can be released by ultrasonication to induce therapy, as described in U.S. Pat. Nos. 5,770,222 and 5,733,572, and WO 684386, each of which expressly incorporated by reference herein in its entirety. A paramagnetic agent may be in the assembly 10 at the region of the linkers 18a, 18b or epitopes 14a, 14b so that it is in contact with the aqueous milieu. An effector molecule 30 may be an echogenic agent such as a microbubble containing one of more fluids, a fluorophore or chromophore capable of emitting or absorbing electromagnetic radiation in the range of about 300-1200nm, a radioactive molecule capable of emitting alpha, beta, or gamma radiation, a paramagnetic agent, X-ray opacification agent, and/or chemotherapeutic agent. The effector molecule may be a paramagnetic agent selected from Gd-DTPA, Gd-DOTA, Gd-DTPA-bis (methoxyethyl) amide, and Mn-EDTA.

In one embodiment, agent 30 is an echogenic agent, fluorophore or chromophore capable of absorbing or emitting light in the range of 300 to 1200 nm, a radiopharmaceutical agent such as diethylenetriamine pentaacetic acid (DTPA) or 1,4,7,10-tetraazacyclododecane-N,N', N'', N'''-tetraacetic acid (DOTA), chelates of beta and gamma emitting isotopes such as Lu, Sm, In, Ru, Tc; cytotoxic agents including, but not limited to, fluorouracil, fluorouridine, etc., and/or sulfa antibiotics including, but not limited to N'-(w-thiazolyl)sulfanilamide, sulfmethoxazole, sulfisoxazole, and sulfisomidine.

In another embodiment, agent 30 is an echogenic water insoluble perfluoropropane or perfluorobutane gas, or is one or more of sulfur hexafluoride, tetrafluoromethane, hexafluoroethane, octafluoropropane, decafluorobutane, dodecafluoropentane, and perfluorohexane. The echogenic agents include mixtures of these gases with a common gas, or mixture of gases such as nitrogen, oxygen, helium, neon, argon, xenon, and carbon dioxide. Superheated fluids or azeotropes of fluorocarbons and perfluorocarbons may be used. Agent 30 may be an optical tracer, such as fluoresceins, rhodamines, cyanines, indocyanines (e.g., indocyanine green), squaraines, phenothiazines, porphyrins, and azo compounds.

In yet another embodiment, the agent 30 may be a bioactive molecule, such as E, P, and L selectins, selectin mimetics, hyaluronic acid, heparin, CD44, ICAM 1, and the like. In this case, the affinity binding sites 15a, 15b in the target 17 generally belong to the class of carbohydrate receptors which are found, for example, on vascular endothelial cells, leukocytes, or platelets.

The structure 13 of the OMMC assembly 10 may be constructed by methods known to one skilled in the art including, but not limited to, micelles, liposomes, emulsions, microparticles, microbubbles, vesicles bounded by uni- or multi-lamellar membranes, nano- and micro-particles, nano- and micro-aggregates, nano- and micro-envelopes, and living cells. In one embodiment, a unilamellar structure surrounds a fluid-filled core, such as a gas/liquid emulsion (bubble). In another embodiment, the lamellar structure 13 is a hybrid containing some amount of waxy substance or polymer that is blended with binding compounds 16a, 16b to form the anchoring regions 12a, 12b. Methods of formation include, but are not limited to, use of an ultrasound microfluidizer, use of a colloid mill, ultramixing, and the like as described in U.S. Pat. Nos. 5,510,118; 5,543,133; and 5,552,133, each of which is expressly incorporated by reference herein in its entirety.

The size of the assembly 10 can be varied according to the type of application contemplated. The size of the assembly 10 may, in one embodiment, be less than 5 microns. In another embodiment, the size of the assembly may range from 1 nm to $10^4$ nm, and can be controlled by known methods, as described in U.S. Pat. No. 6,001,335, which is expressly incorporated by reference herein in its entirety.

The inventive compositions have broad clinical utility. Uses include, but are not limited to, diagnostic imaging of tumors, of inflammation (both noninfectious and infectious), and of impaired vasculature; laser guided endoscopic examination of lesion sites; diagnostic imaging using ultrasound, magnetic resonance, radiographic and optical imaging procedures, and photodynamic therapy and chemotherapy of tumors and infection. Other potential but not limiting uses for targeted specific binding are vascular imaging of the endothelium, imaging of neo-vascularized and inflamed tissue, imaging changes in the circulation in or around necrotic tissue, detection of metastases due to the heterogeneous expression of target molecules, and alleviation of angiogenesis inflammation after re-vascularization of infarcted tissue after stenosis removal.

The OMMC assembly 10 can be formulated into diagnostic or therapeutic compositions for enteral, parenteral, or oral administration. These physiologically acceptable compositions contain an effective amount of an OMMC assembly 10, along with conventional physiological carriers and/or excipients appropriate for the type of administration contemplated. As one example, parenteral administration may advantageously contain a sterile aqueous solution or suspension of assemblies 10 having a concentration in the range of about 0.1 $\mu M$ to about 10 mM (from about $10^6$ to about $10^{10}$ particles/mL). Parenteral formulations may have an assembly 10 concentration from about 100 $\mu M$ to about 2 mM. Such solutions also may contain pharmaceutically acceptable buffers, emulsifiers, surfactants, and, optionally, electrolytes such as sodium chloride. As another example, enteral administration may vary widely, as is well known in the art. In general, such formulations are liquids which include an effective amount of the OMMC assembly 10 in an aqueous solution or suspension. Enteral composition may optionally include buffers, surfactants, emulsifiers, thixotropic agents, and the like. Compositions for oral administration may also contain flavoring agents and other ingredients for enhancing their organoleptic qualities.

The compositions are administered in doses effective to achieve the desired diagnostic and/or therapeutic objective. Such doses may vary widely, depending upon the particular OMMC assembly 10 employed, the organs or tissues to be examined, the equipment employed in the clinical procedure, and the like. The type of equipment needed may also vary widely, depending on the type of imaging modality contemplated.

The following examples serve to illustrate some aspects of the invention.

EXAMPLE 1

Preparation of OMMC Assembly Having One Binding Domain and a Terminal Carboxylate Binding Region, and Containing Gas (Docosanoate ($C_{21}CO_2$—); Octacosanoate ($C_{27}CO_2$—); and Succinylated PEG[100]Stearate Formulated with n-Perfluorobutane)

To an 8 dram (29.6 mL) vial was added docosanoic acid (10.0 mg, Sigma, ~99%); octacosanoic acid (10 mg, Aldrich, ~98%) and 22 mg of succinylated PEG[100]stearate weighed on a Mettler® analytical balance. The mixture was dissolved into about 1 mL of dichloromethane (distilled Mallinckrodt Ultimar®) using mild heating. Dichloromethane was completely removed by the application of heat under a flow of nitrogen (Air Products, High Purity Grade). Excess sodium hydrogen carbonate (about 100 mg, Aldrich, ~99.7%) was placed in the flask along with 10 mL of 0.9% sodium chloride solution used for irrigation (Baxter, USP).

The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. An intensity level of 5 was applied for 2 minutes and 30 seconds. The sample, at about 70° C., was taken out of the sound box so as to cool the vial contents under a flow of tap water to a temperature below about 50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds, and then was increased to a power setting of 7 for 10 seconds. The vial containing a thick white suspension of gas microenvelopes was capped and allowed to cool in a room temperature water bath.

After centrifugation at 1,000×g (2,000 rpm) for 1 minute, the liquid phase (bottom), containing excess matrix material, was completely replaced with a decafluorobutane-saturated 0.9% sodium chloride solution. A resuspension procedure followed by centrifugation was repeated two additional times. A 30 mL plastic syringe barrel fitted with a two-way valve was filled with decafluorobutane (97%, Pfalz & Bauer, Inc.). The sample was suspended thoroughly and poured into the syringe barrel. A stopper was fitted onto the top of the syringe barrel. The sample was allowed to stand for ten minutes. The lower 5 mL was drained into a 10 mL syringe vial filled with decafluorobutane and sealed. A sample was taken for Coulter® analysis and was refrigerated as much as possible.

EXAMPLE 2

Preparation of OMMC Assembly with One Binding Domain and a Terminal Galactosamide Binding Region, and Containing Gas (Docosanoate ($C_{21}CO_2$—); Octacosanoate ($C_{27}CO_2$—); and Octahexadecanoyl[Poly(Ethylene Glycol) 5,000]Succinamic-Galactosyl Amide Formulated with n-Perfluorobutane)

To an 8 dram (29.6 mL) vial was added docosanoic acid (10.0 mg, Sigma, ~99%); octacosanoic acid (10 mg, Aldrich, ~98%) and 22 mg of octahexadecanoyl[poly(ethylene glycol) 5,000]succinamicgalactosyl amide (prepared by the reaction of succinylated PEG[100]stearate, DCC and D-galactosamine (Aldrich)) weighed on a Mettler® analytical balance. The mixture was dissolved into about 1 mL dichloromethane (distilled Mallinckrodt Ultimar®) using mild heating. The dichloromethane was completely removed by the application of heat under a flow of nitrogen (Air Products, High Purity Grade). Excess sodium hydrogen carbonate (~100 mg, Aldrich®, 99.7%) was placed in the flask along with 10 mL of 0.9% sodium chloride solution used for irrigation (Baxter, USP).

The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample, at about 70° C., was taken out of the sound box so as to cool the vial contents under a flow of tap water to a temperature below about 50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds, and then was increased to a power setting of 7 for 10 seconds. The vial of thick white suspension of gas microenvelopes was capped and allowed to cool in a room temperature water bath.

After centrifugation at 1,000×g (2,000 rpm) for 1 minute, the liquid phase (bottom) containing excess matrix material was completely replaced with a decafluorobutane-saturated 0.9% sodium chloride solution. A resuspension procedure followed by centrifugation was repeated two additional times. A 30 cc plastic syringe barrel fitted with a two-way valve was filled with decafluorobutane (97%, Pfalz & Bauer, Inc.). The sample was suspended thoroughly and poured into the syringe barrel. A stopper was fitted onto the top of the syringe barrel. The sample was allowed to stand for ten minutes. The lower 5 mL was drained into a 10 mL syringe vial filled with decafluorobutane and sealed. A sample was taken for Coulter® analysis and was refrigerated as much as possible.

EXAMPLE 3

Preparation of OMMC Assembly with Two Binding Domains (Terminal Carboxylate, Terminal Galactosamide) and Containing Gas (Docosanoate ($C_{21}CO_2$—); Octacosanoate ($C_{27}CO_2$—); Succinylated PEG[100]Stearate and Octahexadecanoyl[Poly (Ethylene Glycol) 5,000]Succinamic-Galactosyl Amide Formulated with n-Perfluorobutane).

To an 8 dram (29.6 mL) vial was added docosanoic acid (10.0 mg, Sigma, ~99%); octacosanoic acid (10 mg, Aldrich, ~98%), 11 mg of octahexadecanoyl[poly(ethylene glycol) 5,000]succinamicgalactosyl amide (prepared by the reaction of succinylated PEG[100]stearate, DCC and D-galactosamine (Aldrich)), and 11 mg of succinylated PEG[100]stearate weighed out on a Mettler® analytical balance. The mixture was dissolved into about 1 mL dichloromethane (distilled Mallinckrodt Ultimar®) using mild heating. The dichloromethane was completely removed by the application of heat under a flow of nitrogen (Air Products, High Purity Grade). Excess sodium hydrogen carbonate (~100 mg, Aldrich, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample, at about 70° C., was taken out of the sound box so as to cool the vial contents under a flow of tap water to a temperature below about 50° C. as measured by a FLUKE® 52 K/J thermometer fitted with a K thermocouple.

The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds, and then increased to a power setting of 7 for 10 seconds. The vial of thick white suspension of gas microenvelopes was capped and allowed to cool in a room temperature water bath. The liquid phase (bottom) containing excess matrix material was completely replaced with decafluorobutane saturated 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at about 70° C. was taken out of the sound box so as to cool the vial contents under a flow of tap water to a temperature below about 50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds, and then increased to a power setting of 7 for 10 seconds. The vial of thick white suspension of gas microenvelopes was capped and allowed to cool in a room temperature water bath. The liquid phase (bottom) containing excess matrix material was completely replaced with decafluorobutane saturated 0.9% sodium chloride solution after centrifugation at 1,000×g (2,000 rpm) for 1 minute. Resuspension procedure followed by centrifugation was repeated two additional times.

A 30 mL plastic syringe barrel fitted with a two-way valve was filled with decafluorobutane (97%, Pfalz & Bauer, Inc.). The sample was suspended thoroughly and poured into the syringe barrel. A stopper was fitted onto the top of the syringe barrel. The sample was allowed to stand for ten minutes. The lower 5 mL was drained into a 10 mL syringe vial filled with decafluorobutane and sealed. A sample was taken for Coulter® analysis, and was kept refrigerated as much as possible.

EXAMPLE 4

Binding of OMMC Assemblies

The assemblies prepared in Examples 1, 2, and 3 were incubated over a 30 minute period with stirring in the presence of a semi-confluent monolayer of human umbilical cord endothelial cells (HUVEC), (ATCC CRL-1730). The cells were placed into adjacent wells in the presence of media with and without heparin present. Media was removed and the cells were washed.

Figure 4:
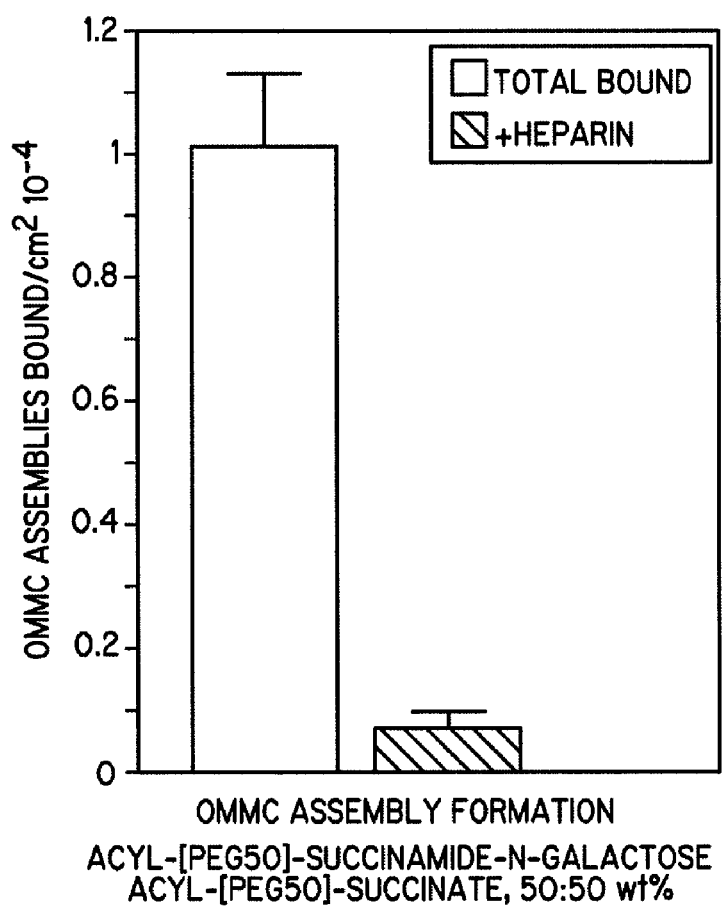
FIG. 4 shows results of composite OMMC ensemble binding to human endothelial cells.

After the 30 minute incubation, the cells were examined microscopically (200×) with phase contrast for binding of the assemblies. Little binding was noted with assemblies containing only one binding domain of charged (sulfate anion alone) carboxylate (data not shown). Some binding occurred with assemblies containing surface N-acyl-mannoside or -galactoside terminated microenvelopes (data not shown). As shown in FIG. 4, binding was greatly increased, and there was excellent surface coverage of activated cells, with assemblies containing the combination of sulfate and N-acyl-mannoside or N-acyl-galactoside composite microenvelopes.

In all cases, binding was substantially blocked by the presence of heparin or hyaluronic acid oligosaccharides. This is likely due to heparin or hyaluronic acid oligosaccharide in free solution blocking the binding of the assemblies by competing for complementary affinity sites on the cell membrane or extracellular matrix.

EXAMPLE 5

Preparation of Gas-Filled Microenvelopes Comprised of Docosanoate ($C_{21}CO_2$—); Octacosanoate ($C_{27}CO_2$—); and Octahexadecanoyl[Poly(Ethylene Glycol) 5,000]Succinamic-Galactosyl Amide and Sulfated PEG[100]Stearate Formulated with n-Perfluorobutane To an 8 dram (29.6 mL) vial was added docosanoic acid (10.0 mg, Sigma, ~99%); octacosanoic acid (10 mg, Aldrich, ~98%) and 10 mg each of octahexadecanoyl[poly(ethylene glycol) 5,000]succinamicgalactosyl amide (prepared by the reaction of succinylated PEG[100]stearate, DCC and D-galactosamine (Aldrich)) and sulfated PEG[100]stearate (prepared by the reaction of PEG[100]stearate, DCC and sulfuric acid) weighed on a Mettler® analytical balance. The mixture was dissolved into about 1 mL acetone (distilled Mallinckrodt Ultimar®) using mild heating. The acetone was completely removed by the application of heat under a flow of nitrogen (Air Products, High Purity Grade). Excess sodium hydrogen carbonate (~100 mg, Aldrich, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. An intensity level of 5 was applied for 2 minutes and 30 seconds. The sample, at about 70° C., was taken out of the sound box so as to cool the vial contents under a flow of tap water to a temperature below about 50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds, and then was increased to a power setting of 7 for 10 seconds. The vial of thick white suspension of gas microenvelopes was capped and allowed to cool in a room temperature water bath.

After centrifugation at 1,000×g (2,000 rpm) for 1 minute, the liquid phase (bottom) containing excess matrix material was completely replaced with a decafluorobutane-saturated 0.9% sodium chloride solution. A 30 cc plastic syringe barrel fitted with a two-way valve was filled with decafluorobutane (97%, Pfalz & Bauer, Inc.). The sample was suspended thoroughly and poured into the syringe barrel. A stopper was fitted onto the top of the syringe barrel. The sample was allowed to stand for twenty minutes. The lower 5 mL was drained into a 10 mL syringe vial filled with decafluorobutane and sealed. The sample was kept refrigerated as much as possible.

EXAMPLE 6

Preparation of Gas-Filled Microenvelopes Comprised of Docosanoate ($C_{21}CO_2$—); Octacosanoate ($C_{27}CO_2$—); and Octahexadecanoyl[Poly(Ethylene Glycol) 5,000]Succinamic-Mannosyl Amide Formulated with n-Perfluorobutane To an 8 dram (29.6 mL) vial was added docosanoic acid (10.0 mg, Sigma, ~99%); octacosanoic acid (10 mg, Aldrich, ~98%) and 20 mg of octahexadecanoyl[poly(ethylene glycol) 5,000]succinamicmannosyl amide weighed on a Mettler® analytical balance. The procedure as described in Example 5 was followed. The resultant sample was kept refrigerated as much as possible.

EXAMPLE 7

Preparation of Gas-Filled Microenvelopes Comprised of Docosanoate ($C_{21}CO_2$—); Octacosanoate ($C_{27}CO_2$—); and Octahexadecanoyl[Poly(Ethylene Glycol) 5,000]Succinamic-Mannosyl Amide and Sulfated PEG[100]Stearate Formulated with n-Perfluorobutane To an 8 dram (29.6 mL) vial was added docosanoic acid (10.0 mg, Sigma, ~99%); octacosanoic acid (10 mg, Aldrich, ~98%) and 10 mg each of octahexadecanoyl[poly(ethylene glycol) 5,000]succinamicmannosyl amide (prepared by the reaction of succinylated PEG[100]stearate, DCC and D-mannosamine (Aldrich)) and sulfated PEG[100]stearate (prepared by the reaction of PEG[100]stearate, DCC and sulfuric acid) weighed out on a Mettler® analytical balance. The procedure as described in Example 5 was followed. The resultant sample was kept refrigerated as much as possible.

EXAMPLE 8

Preparation of Gas-Filled Microenvelopes Comprised of Docosanoate ($C_{21}CO_2$—); Octacosanoate ($C_{27}CO_2$—); and Sulfated PEG[100]Stearate Formulated with n-Perfluorobutane To an 8 dram (29.6 mL) vial was added docosanoic acid (10.0 mg, Sigma, ~99%); octacosanoic acid (10 mg, Aldrich, ~98%) and 20 mg of sulfated PEG[100]stearate weighed on a Mettler® analytical balance. The procedure as described in Example 5 was followed. The resultant sample was kept refrigerated as much as possible.

EXAMPLE 9

Binding of the Gas-Filled Microenvelopes to Activated Endothelial Cells (HUVEC)

The microenvelopes (bubbles) prepared in Examples 5, 6, 7, and 8 were incubated over a 30-minute period with stirring in the presence of a monolayer of human endothelial cells (HUVEC, human umbilical cord endothelial cells, ATCC CRL-1730). The three samples generated as described in Examples 5-8 were incubated in adjacent wells in the presence of media with and without heparin present.

After removing the media, washing, and microscopic examination (400×) with phase contrast, little binding was noted with only charged (sulfate anion alone) microenvelopes. Some binding occurred with surface with N-acyl-mannoside or -galactoside terminated microenvelopes. Greatly increased, excellent surface coverage of bubbles binding to activated cells was observed with the combination of sulfated and N-acyl-mannoside or -galactoside composite microenvelopes. The binding in all cases was completely blocked by the presence of heparin.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A biocompatible organized mobile multicomponent conjugate (OMMC) comprising:
   (A) a lamellar structure comprising $R^2O_2CCH_2(CHY)CO_2R^2$, wherein:
      (1) $R^2$ is an alkyl radical containing 16-24 carbon atoms;
      (2) Y is selected from —$(CH_2)_k$—X, —$NHCO(CH_2)_k$—X, —$OCO(CH_2)_k$—X, and —$CH_2OCO(CH_2)_2$—$CO_2$—;
      (3) X is selected from carboxylate, sulfonate, sulfate, and phosphate, and phosphonate; and
      (4) k is 1-6; and
   (B) a first binding compound and a second binding compound, each of which is anchored to the lamellar structure, the first binding compound capable of binding to an exogenous first affinity site, and the second binding compound capable of binding to an exogenous second affinity site, wherein the first and second binding compounds are mobile and self-adjust relative to the lamellar structure to allow for cooperative binding of the first and second binding compounds to said first and second affinity sites, respectively, wherein each binding compound independently comprises:

(1) an anchor region that anchors the binding compound to the lamellar structure, the anchor region being selected from $CH_3(CH_2)_a$—W, $CH_3(CH_2)_a$—O—$(CH_2)_b$—W, $CH_3(CH_2)_a$—S—$(CH_2)_b$—W, $R^1O_2CCH_2(CHW)CO_2R^1$, $CF_3(CH_2)_a$—W, $CF_3(CF_2)_a$—W, $CF_3(CF_2)_aCH_2CH_2$—W, $CF_3(CF_2)_a$—O—$(CH_2)_b$—W, and $CH_3(CH_2)_a$—S—S—$(CH_2)_b$—W, wherein:

(a) each of a and b ranges from 16 to 32, inclusive;
(b) W is selected from —O—, —CO—, —$CO_2$—, —OCO—, —$O_2CO$—, —S—, —SO—, —$SO_2$—, —NH—, —NHCO—, —NHCS—, —$NHSO_2$—, —$PO_2H$—, —$OPO_2H$—, —$PO_2$—, and —$OPO_2$—; and
(c) $R^1$ is an alkyl radical containing 16 to 24 carbon atoms; and (2) a binding region selected from amino acids, peptides, peptidomimics, monosaccharides, disaccharides, oligosaccharides, sialic acid, carminic acid, and anionic compounds selected from —$(CH_2)_d$—$CO_2$-, —$(CH_2)_d$—$SO_3$-, —$(CH_2)_d$—$OSO_3$-, —$(CH_2)_d$—$PO_3$=, —$(CH_2)_d$—$OPO_3$=, —Ar—$SO_3$-, DTPA, EDTA, DOTA, and EGTA, wherein d ranges from 1 to 10, inclusive; and (3) a linker that connects the anchor region to the binding region, the linker being selected from polysorbates, polyglycerols, polypeptides, polynucleotides, polysaccharides, polyvinylpyrrolidones, polyvinylalcohols, polyethyleneglycols, polyglycolate, polylactate, and copolymers of any of the members of this group.

2. The conjugate of claim 1, wherein Y is $NHCO(CH_2)_k$—X.
3. The conjugate of claim 2, wherein X is carboxylate.
4. The conjugate of claim 1, wherein X is carboxylate.
5. The conjugate of claim 1, wherein the anchor region of the first binding compound, the second binding compound, or each of the first and second binding compounds is $CH_3(CH_2)_a$—W.
6. The conjugate of claim 5, wherein W is —O—.
7. The conjugate of claim 5, wherein W is —CO—.
8. The conjugate of claim 5, wherein W is —$CO_2$—.
9. The conjugate of claim 5, wherein W is —NH—.
10. The conjugate of claim 5, wherein W is —$O_2CO$—.
11. The conjugate of claim 5, wherein W is —NHCO—.
12. The conjugate of claim 5, wherein W is —S—.
13. The conjugate of claim 1, wherein the anchor region of the first binding compound, the second binding compound, or each of the first and second binding compounds is $R^1O_2CCH_2(CHW)CO_2R^1$.
14. The conjugate of claim 13, wherein W is —O—.
15. The conjugate of claim 13, wherein W is —CO—.
16. The conjugate of claim 13, wherein W is —$CO_2$—.
17. The conjugate of claim 13, wherein W is —NH—.
18. The conjugate of claim 13, wherein W is —$O_2CO$—.
19. The conjugate of claim 13, wherein W is —NHCO—.
20. The conjugate of claim 13, wherein W is —S—.

21. The conjugate of claim 1, wherein the anchor region of the first binding compound, the second binding compound, or each of the first and second binding compounds is $CH_3(CH_2)_a$—O—$(CH_2)_b$—W.
22. The conjugate of claim 21, wherein W is —O—.
23. The conjugate of claim 21, wherein W is —CO—.
24. The conjugate of claim 21, wherein W is —$CO_2$—.
25. The conjugate of claim 21, wherein W is —NH—.
26. The conjugate of claim 21, wherein W is —$O_2CO$—.
27. The conjugate of claim 21, wherein W is —NHCO—.
28. The conjugate of claim 21, wherein W is —S—.
29. The conjugate of claim 1, wherein the binding region of the first binding compound, the second binding compound, or each of the first and second binding compounds is an amino acid.
30. The conjugate of claim 1, wherein the binding region of the first binding compound, the second binding compound, or each of the first and second binding compounds is a monosaccharide.
31. The conjugate of claim 30, wherein the binding region of the first binding compound, the second binding compound, or each of the first and second binding compounds is selected from C monosaccharides and O monosaccharides.
32. The conjugate of claim 1, wherein the binding region of the first binding compound, the second binding compound, or each of the first and second binding compounds is a disaccharide.
33. The conjugate of claim 1, wherein the binding region of the first binding compound, the second binding compound, or each of the first and second binding compounds is sialic acid.
34. The conjugate of claim 1, wherein the binding region of the first binding compound, the second binding compound, or each of the first and second binding compounds is a glycoside of a monosaccharide or sialic acid.
35. The conjugate of claim 1, wherein the binding region of the first binding compound, the second binding compound, or each of the first and second binding compounds is a monosaccharide selected from mannose, glucose, fucose, and galactose.
36. The conjugate of claim 1, wherein the binding region of the first binding compound, the second binding compound, or each of the first and second binding compounds is a monosaccharide selected from glucosamine, mannosamine, and galactosamine.
37. The conjugate of claim 1, wherein the binding region of the first binding compound, the second binding compound, or each of the first and second binding compounds is DTPA.
38. The conjugate of claim 1, wherein the binding region of the first binding compound, the second binding compound, or each of the first and second binding compounds is DOTA.
39. The conjugate of claim 1, wherein the binding region of the first binding compound, the second binding compound, or each of the first and second binding compounds is a peptide.
40. The conjugate of claim 1, wherein the binding region of the first binding compound, the second binding compound, or each of the first and second binding compounds is independently selected from —$(CH_2)_d$—$CO_2$-, —$(CH_2)_d$—$SO_3$-, —$(CH_2)_d$—$OSO_3$-, —$(CH_2)_d$—$PO_3$=, —$(CH_2)_d$—$OPO_3$=, and —Ar—$SO_3$-.
41. The conjugate of claim 1, wherein the binding region of the first binding compound, the second binding compound, or each of the first and second binding compounds is —$(CH_2)_d$—$CO_2$-.
42. The conjugate of claim 1, wherein the binding region of the first binding compound, the second binding compound, or each of the first and second binding compounds is —$(CH_2)_d$—$OSO_3$-.

43. The conjugate of claim 1, wherein the binding region of the first binding compound, the second binding compound, or each of the first and second binding compounds is —$(CH_2)_d$—$OPO_3$=.

44. The conjugate of claim 1, wherein the linker of the first binding compound, the second binding compound, or each of the first and second binding compounds is a polyvinylpyrrolidone.

45. The conjugate of claim 1, wherein the linker of the first binding compound, the second binding compound, or each of the first and second binding compounds is a polyethyleneglycol.

46. The conjugate of claim 45, wherein the polyethyleneglycol has a molecular weight in the range of 1,000 to 4,000.

47. The conjugate of claim 45, wherein the linker of the first binding compound, the second binding compound, or each of the first and second binding compounds is poly(ethyleneglycol)$_p$, wherein p is from 40 to 150.

48. The conjugate of claim 1, wherein the linker of the first binding compound, the second binding compound, or each of the first and second binding compounds is polyglycolate.

49. The conjugate of claim 1, wherein the linker of the first binding compound, the second binding compound, or each of the first and second binding compounds is polylactate.

50. The conjugate of claim 1, wherein the linker of the first binding compound, the second binding compound, or each of the first and second binding compounds is a copolymer of polyglycolate or a copolymer of polylactate or a copolymer of polyglycolate and polylactate.

51. The conjugate of claim 1, wherein the first binding compound or the second binding compound has a dissociation constant ($K_d$) value equal to or greater than about 100 nM.

52. The conjugate of claim 1, wherein each of the first and second binding compounds has a dissociation constant ($K_d$) value equal to or greater than about 100 nM.

53. The conjugate of claim 1, wherein the first binding compound or the second binding compound has a dissociation constant ($K_d$) value of at least about 100 nM.

54. The conjugate of claim 1, wherein each of the first and second binding compounds has a dissociation constant ($K_d$) value of at least about 100 nM.

55. The conjugate of claim 1, wherein the first binding compound is the same as the second binding compound.

56. The conjugate of claim 1, further comprising:
an effector molecule attached to the lamellar structure.

57. The conjugate of claim 1, wherein the lamellar structure has a void defined therein, and the conjugate further comprises an effector molecule contained within the void of the lamellar structure.

58. The conjugate of claim 1, further comprising:
an effector molecule incorporated within the lamellar structure.

59. The conjugate of any one of claims 56-58, wherein the effector molecule is a cytotoxic agent.

60. The conjugate of any one of claims 56-58, wherein the effector molecule is a cytotoxic agent selected from fluorouracil and fluorouridine.

61. The conjugate of any one of claims 56-58, wherein the effector molecule is a paramagnetic agent.

62. The conjugate of any one of claims 56-58, wherein the effector molecule is a paramagnetic agent selected from Gd-DTPA, Gd-DOTA, Gd-DTPA-bis(methoxyethyl)amide, and Mn-EDTA.

63. The conjugate of any one of claims 56-58, wherein the effector molecule is an optical agent.

64. The conjugate of any one of claims 56-58, wherein the effector molecule is an optical agent selected from fluorophores that absorb light in the range of 300- 1200 nm and chromophores that absorb light in the range of 300-1200 nm.

65. The conjugate of any one of claims 56-58, wherein the effector molecule is an optical agent selected from fluoresceins, rhodamines, cyanines, indocyanines, squaraines, phenothiazines, porphyrins, and azo compounds.

66. The conjugate of any one of claims 56-58, wherein the effector molecule is an optical agent selected from fluorescein and indocyanine green.

67. The conjugate of any one of claims 56-58, wherein the effector molecule is a sulfa antibiotic.

68. The conjugate of any one of claims 56-58, wherein the effector molecule is a sulfa antibiotic selected from sulfisoxazole, N'-(w-thiazolyl)sulfanilamide, sulfmethoxazole, and sulfisomidine.

69. The conjugate of any one of claims 56-58, wherein the effector molecule is a radiopharmaceutical agent.

70. The conjugate of any one of claims 56-58, wherein the effector molecule is a radioactive molecule emitting alpha, beta, or gamma radiation.

71. The conjugate of any one of claims 56-58, wherein the effector molecule is a radiopharmaceutical agent that comprises a chelate of a beta emitting isotope or a chelate of a gamma emitting isotope.

72. The conjugate of any one of claims 56-58, wherein the effector molecule is a radiopharmaceutical agent that comprises Lu, Sm, In, Ru, or Tc.

73. The conjugate of any one of claims 56-58, wherein the effector molecule comprises a radionuclide selected from l-123, l-131, Tc-99m, Re-186, Re-188, Sm-152, Ho-155, Bi-202, and Lu-177.

74. The conjugate of any one of claims 56-58, wherein the effector molecule is a radiopharmaceutical agent selected from diethylenetriamine pentaacetic acid (DTPA) or 1,4,7, 10-tetraazacyclododecane-N, N', N'', N'''- tetraacetic acid (DOTA).

75. The conjugate of any one of claims 56-58, wherein the effector molecule is a chemotherapeutic agent.

76. The conjugate of any one of claims 56-58, wherein the effector molecule is selected from hyaluronic acid and heparin.

77. The conjugate of any one of claims 56-58, wherein the effector molecule is an X-ray opacification agent.

78. The conjugate of any one of claims 56-58, wherein the effector molecule is an echogenic agent.

79. The conjugate of claim 1, wherein the lamellar structure comprises a micelle.

80. The conjugate of claim 1, wherein the lamellar structure comprises a liposome.

81. The conjugate of claim 1, wherein the lamellar structure comprises a microparticle.

82. The conjugate of claim 1, wherein the lamellar structure comprises a nanoparticle.

83. The conjugate of any one of claims 1-43, 51-58, and 79-82, wherein the linker of the first binding compound, the second binding compound, or each of the first and second binding compounds is a polynucleotide.

84. The conjugate of any one of claims 1-43, 51-58, and 79-82, wherein the linker of the first binding compound, the second binding compound, or each of the first and second binding compounds is a copolymer of a polynucleotide.

* * * * *

UNITED STATES PATENT AND TRADEMARK OFFICE
CERTIFICATE OF CORRECTION

PATENT NO.         : 8,257,683 B2
APPLICATION NO.    : 12/603402
DATED              : September 4, 2012
INVENTOR(S)        : Gary L. Cantrell and B. Daniel Burleigh Page 1 of 1

It is certified that error appears in the above-identified patent and that said Letters Patent is hereby corrected as shown below:

Claim 1, Column 17; Line 32: "-Ar-SO$_3$-," should read -- -Ar-SO$_3^-$, --

Claim 40, Column 18; Line 57: "-(CH$_2$)$_d$-CO$_2$-, -(CH$_2$)$_d$-SO$_3$-." should read -- -(CH$_2$)$_d$-CO$_2^-$, -(CH$_2$)$_d$-SO$_3^-$ --

Claim 40, Column 18; Line 58: "-(CH$_2$)$_d$-OSO$_3$-," should read -- -(CH$_2$)$_d$-OSO$_3^-$ --

Claim 40, Column 18; Line 59: "-Ar-SO$_3$-." should read -- -Ar-SO$_3^-$ --

Claim 41, Column 18; Line 63: "-CO$_2$-." should read -- -CO$_2^-$. --

Claim 42, Column 18; Line 67: "-OSO$_3$-." should read -- -OSO$_3^-$. --

Claim 73, Column 20; Line 32: "1-123, 1-131" should read -- I-123, I-131 --

Signed and Sealed this
Sixth Day of November, 2012

David J. Kappos
*Director of the United States Patent and Trademark Office*